(12) United States Patent
Naba (10) Patent No.: US 9,119,562 B2
(45) Date of Patent: Sep. 1, 2015

(54) IMAGING CONTROL APPARATUS, OPHTHALMIC IMAGING APPARATUS, IMAGING CONTROL METHOD, AND PROGRAM

(75) Inventor: Takashi Naba, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 12 days.

(21) Appl. No.: 13/546,808

(22) Filed: Jul. 11, 2012

(65) Prior Publication Data

US 2013/0016320 A1 Jan. 17, 2013

(30) Foreign Application Priority Data

Jul. 14, 2011 (JP) .................................. 2011-155870

(51) Int. Cl.
*A61B 3/14* (2006.01)
*A61B 3/10* (2006.01)

(52) U.S. Cl.
CPC ............... *A61B 3/102* (2013.01); *A61B 3/1025* (2013.01)

(58) Field of Classification Search
USPC .................................. 351/205–208, 210, 212
See application file for complete search history.

(56) References Cited

U.S. PATENT DOCUMENTS

| 4,768,874 A | 9/1988 | Webb |
| 2003/0231285 A1 | 12/2003 | Ferguson |
| 2010/0157311 A1 | 6/2010 | Hayashi |
| 2010/0315590 A1* | 12/2010 | Ueno ............................ 351/206 |
| 2011/0205490 A1* | 8/2011 | Murata et al. ................. 351/206 |
| 2012/0154747 A1 | 6/2012 | Makihira |

FOREIGN PATENT DOCUMENTS

JP 2001-70247 A 3/2001

* cited by examiner

*Primary Examiner* — Ricky Mack
*Assistant Examiner* — Mustak Choudhury
(74) *Attorney, Agent, or Firm* — Canon USA, Inc., IP Division (57) ABSTRACT

An imaging control apparatus capable of causing a first imaging unit to capture a fundus image of a subject's eye and causing a second imaging unit to capture a tomographic image of the subject's eye includes a control unit configured to cause the first imaging unit to capture an image of the fundus of the subject's eye in a limited area smaller than the fundus image, a detection unit configured to detect a positional deviation of the fundus of the subject's eye based on an image of the area acquired according to the control, and a correction unit configured to correct an image capturing position of the tomographic image captured by the second imaging unit based on the detected positional deviation.

17 Claims, 6 Drawing Sheets

IMAGING CONTROL APPARATUS, OPHTHALMIC IMAGING APPARATUS, IMAGING CONTROL METHOD, AND PROGRAM

BACKGROUND

Various types of ophthalmic apparatuses employing optical apparatuses are used. For example, optical apparatuses for observing eyes include anterior eye imaging apparatuses, fundus cameras, and confocal scanning laser ophthalmoscopes (SLOs). Especially, an optical coherence tomography apparatus (hereinafter, referred to as OCT apparatus) can acquire high-resolution tomographic images of a sample, and the apparatus has become an essential ophthalmic apparatus used in outpatient clinics specializing in retina care.

The OCT apparatus enables high-sensitivity eye measurement by irradiating a sample with low coherent light, and using an interference system of the reflected light from the sample. Further, the OCT apparatus can acquire high-resolution tomographic images by scanning the sample with the low coherent light. Since the OCT apparatus can capture high-resolution tomographic images of a retina in a fundus of a subject's eye, the OCT apparatus is widely used for an ophthalmic diagnosis for retinas, and the like.

In the ophthalmic diagnosis for retinas, a tomographic image of a retina, which is referred to as a B scan image, captured by an OCT apparatus are generally used. The B scan image is acquired by performing scanning in a depth direction (Z direction) of the retina, which is referred to as A scan, in an X direction for a plurality of times. When comparing with an image of a conventional fundus camera, a state of an inside of the retina can be observed from the B scan image, the B scan is an innovative technique for observing a lesion inside of the retina, especially, for observation of macular degeneration, a macular hole, and the like.

The B-scan image is acquired by only one scanning. However, by scanning the same point for a plurality of times and superimposing the scanned images, a sharp image with less noise can be acquired. However, human eyes move involuntary, which is referred to as involuntary eye movement during fixation. Due to the movement, a target retina involuntary moves while the same point is geometrically scanned, and accordingly, it is difficult to superimpose many images.

United States Patent Application Publication No. 2010-0157311 discusses a device for capturing a plurality of B-scan images in the Y direction to acquire a three-dimensional retinal image is developed. The acquisition of the three-dimensional retinal image contributes to the observation of the extent of a lesion and layers in a retina, especially to the observation of the ganglionic layer of optic nerve that causes glaucoma. However, in the observation, due to the movement of the eyeball, the three-dimensional retinal image may be distorted. To solve this issue, a technique referred to as tracking has been developed. In the tracking technique, a fundus image is captured while tomographic images of the retina are captured, and a feature point such as a branch point of a blood vessel in the fundus image is focused. When the feature point moves, the movement is determined to be the movement of the retina, and the scanning position of the OCT apparatus is changed.

To accurately measure the movement of the eyeball using the fundus image, it is required to perform the processing of extracting the feature point from the fundus image, searching and detecting the feature point in the images to be processed, and calculating an amount of the movement at a high speed. As the feature point in the fundus image, a macula, an optic papillary portion (hereinafter, referred to as an optic papilla), or the like is used. In an affected eye, the macula and the optic papilla are often unclear, and consequently, a blood vessel can be used as the feature point in fundus image. Japanese Patent Application Laid-Open No. 2001-70247 discusses a method for extracting a feature point of a blood vessel.

The apparatuses for capturing a fundus image include fundus cameras and scanning ophthalmoscopes. The fundus camera acquires a fundus image of the whole area at one time. The scanning ophthalmoscope acquires a fundus image by scanning the fundus with a beam. The scanning ophthalmoscope includes the SLO and line-scanning laser ophthalmoscopy (LSLO). The SLO irradiates a laser spot on a fundus, and scans the fundus with a laser beam. The LSLO irradiates and scans a fundus with a linear laser beam. The scanning ophthalmoscopes are considered to be able to provide high-quality (high-resolution, high-luminance) images while its image capturing time is longer than that of the fundus camera. Detailed configuration of the LSLO is discussed in U.S. Pat. No. 4,768,874 and United States Patent Application publication No. 2003-0231285. Generally, to measure the movement of an eyeball, a feature point is to be detected. Consequently, a scanning ophthalmoscope capable of performing high-quality continuous shooting is used.

However, in the simultaneous imaging by the OCT apparatus for tracking and by the scanning ophthalmoscope described above, the imaging light of the OCT apparatus and the imaging light of the scanning ophthalmoscope simultaneously enters the eye to be observed. Then, the light amount entering the eye increases. On the other hand, the upper limit of the incident light amount allowed for the eye observation is determined by the International Organization for Standardization (ISO), and other organizations. Accordingly, the imaging light amount of the OCT apparatus is to be adjusted to a low amount. This results in deterioration in image quality such as decrease in signal-to-noise (S/N) ratios.

SUMMARY

According to some embodiments of the present invention, an imaging control apparatus capable of causing a first imaging unit to capture a fundus image of a subject's eye and causing a second imaging unit to capture a tomographic image of the subject's eye includes a control unit configured to cause the first imaging unit to capture an image of the fundus of the subject's eye in a limited area smaller than the fundus image, a detection unit configured to detect a positional deviation of the fundus of the subject's eye based on an image of the area acquired according to the control, and a correction unit configured to correct an image capturing position of the tomographic image captured by the second imaging unit based on the detected positional deviation.

Further features and aspects of the embodiment will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, and features, together with the description, serve to explain the principles of the invention.

DESCRIPTION OF THE EMBODIMENTS

Various exemplary embodiments, features, and aspects will be described in detail below with reference to the drawings.

Figure 1:
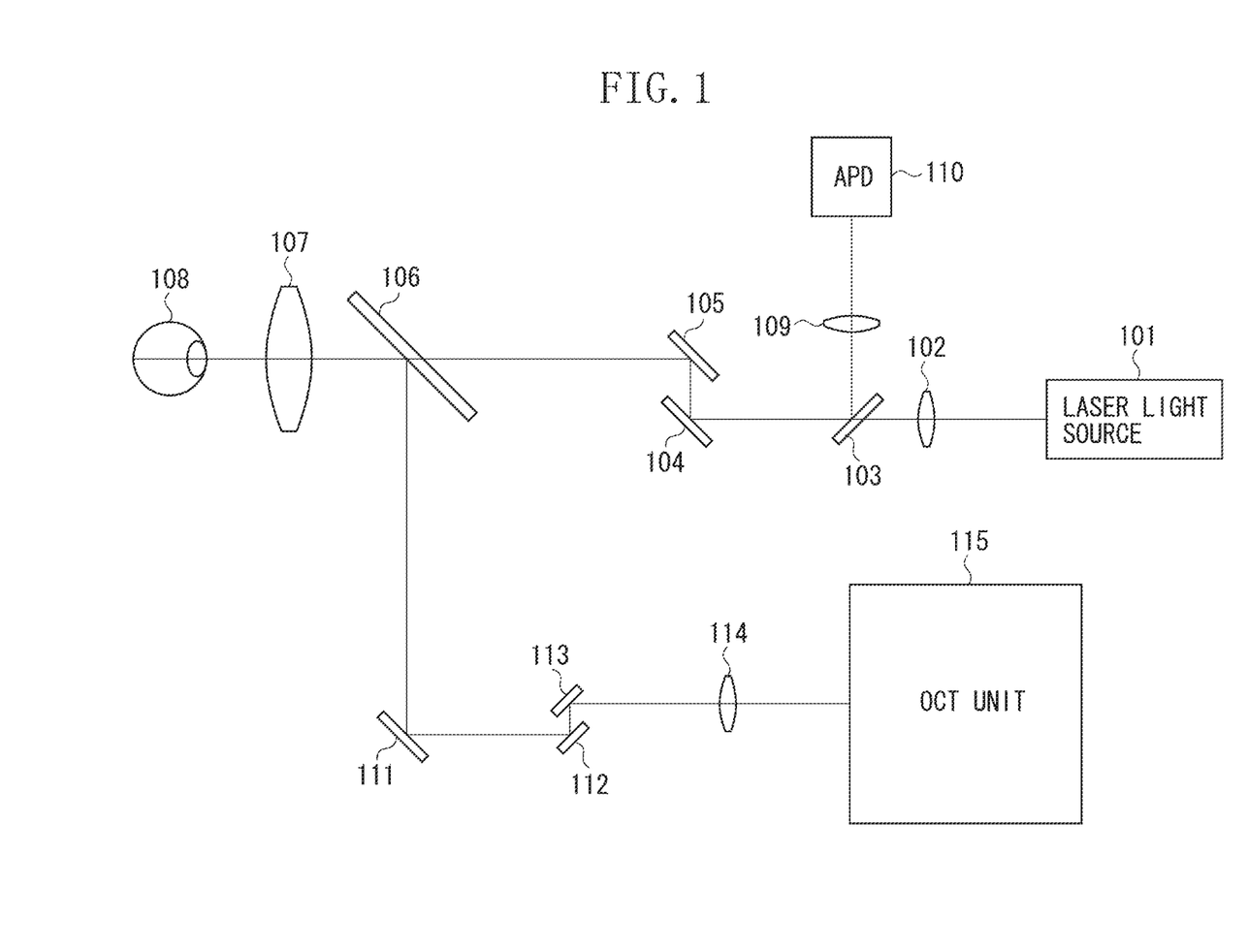
FIG. 1 is a view illustrating a configuration of a fundus image capturing apparatus according to an exemplary embodiment of the present invention.

FIG. 1 illustrates a configuration of a fundus image capturing apparatus (ophthalmic imaging apparatus) according to an exemplary embodiment of the present invention. With reference to FIG. 1, a scanning laser ophthalmoscope (SLO) for implementing a fundus observation method is described. In FIG. 1, a laser light source 101 can be a semiconductor laser or a super luminescent diode (SLD) light source. To reduce glare given to a subject and to maintain a resolution in the fundus observation, it is preferable to use a laser light source of a wavelength within the near-infrared region of 700 nm to 1000 nm. In the present exemplary embodiment, it is assumed that a semiconductor laser of the wavelength of 780 nm is used, and a light amount can be changed by control voltage.

A laser beam emitted from the laser light source 101 is collimated by a collimator lens 102, passes through a hole at the center of a perforated mirror 103, and further passes through an SLO-X scanner 104 and an SLO-Y scanner 105. The laser beam further passes through abeam splitter 106 and an eyepiece lens 107, and enters a subject's eye 108. According to the present exemplary embodiment described below, an eye axis direction is defined as a Z coordinate, a horizontal direction with respect to a fundus image is defined as an X coordinate, and a vertical direction thereof is defined as a Y coordinate.

The beam entered the subject's eye 108 irradiates the fundus in a dot-like state. The beam is reflected or scattered on the fundus of the subject's eye 108, passes through the same optical path and returns to the perforated mirror 103. The reflected or scattered light is reflected by the perforated mirror 103, and received by an avalanche photodiode (APD) 110 via a lens 109. Then, in the APD 110, a signal proportionate to a reflection/scattering strength at the point on the fundus is acquired. In addition, the SLO-X scanner 104 and the SLO-Y scanner 105 perform raster scan, and a two-dimensional image of the fundus can be acquired.

Figure 2:
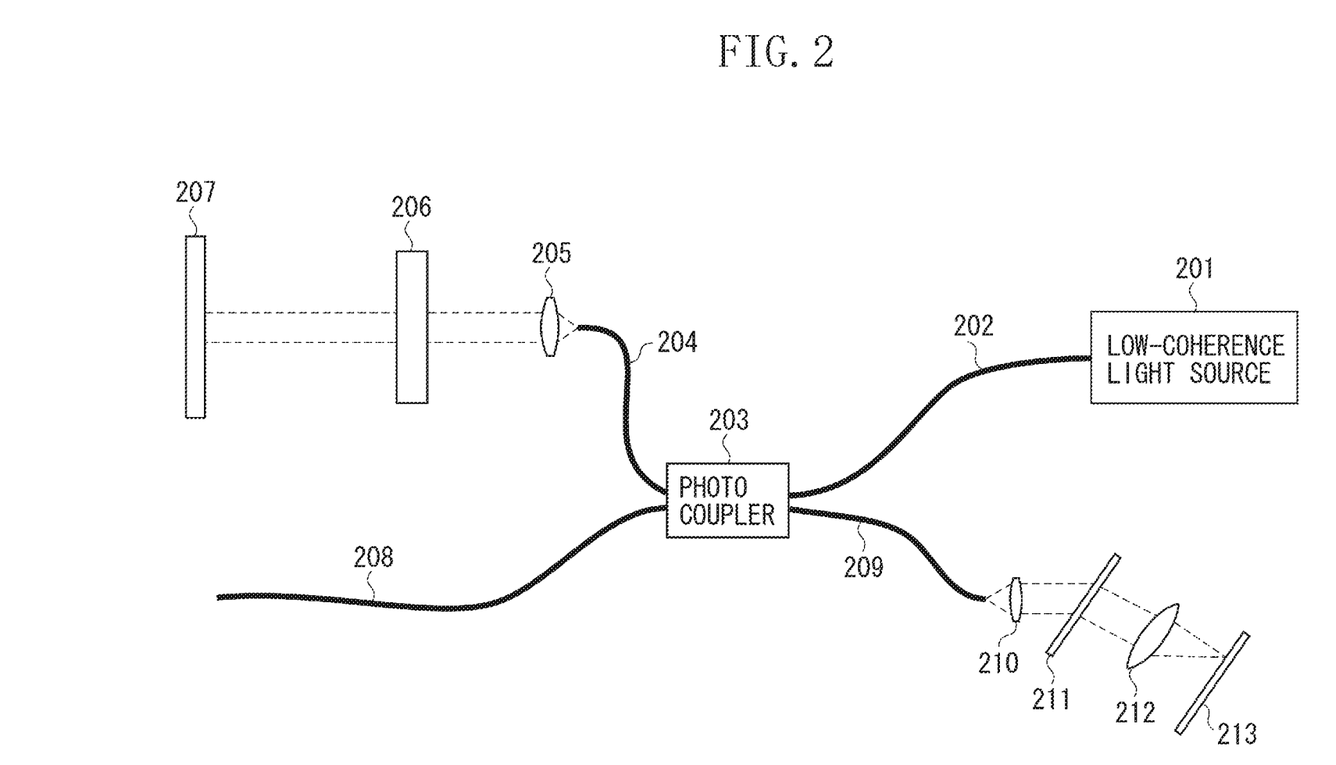
FIG. 2 is a view illustrating a configuration of an OCT unit.

With reference to FIG. 2, an optical coherence tomography (OCT) unit 115 illustrated in FIG. 1 is described. FIG. 2 illustrates a configuration of the OCT unit 115. The OCT unit 115 divides the low-coherence light into reference light and observation light. The OCT unit 115 superimposes the observation light via the subject's eye 108 and the reference light via a reference object to generate interference light, and outputs a signal by dispersing the interference light. The dispersed signal is input into a central processing unit (CPU) 301 described below. The CPU 301 analyzes the dispersed signal and forms a tomographic image or a three-dimensional image of the fundus.

In FIG. 2, a low-coherence light source 201 includes a broadband light source that can output the low-coherence light. In the present exemplary embodiment, an SLD is employed as the broadband light source. The low-coherence light includes the light of a wavelength range in the near-infrared region, and has a coherence length of several tens of micrometers. For example, the low-coherence light has a wavelength within the range from about 800 nm to 900 nm.

The low-coherence light output from the low-coherence light source 201 is guided to an optical coupler 203 via an optical fiber 202. The optical fiber 202 typically employs a single mode fiber. The optical coupler 203 divides the low-coherence light into the reference light and the observation light. The reference light generated by the optical coupler 203 is guided by the optical fiber 204 and collimated by a collimator lens 205. Then, the collimated reference light passes through a glass block 206 that functions as a dispersion compensation means for compensating the dispersion characteristics of the reference light and the observation light, and is reflected by a reference mirror 207. The reflected reference light passes through the same optical path, and enters the optical fiber 204.

The reference mirror 207 can move in the direction the reference light proceeds. Accordingly, adjustment of the length of the eye axis of the subject's eye 108, and a distance between the eyepiece lens 107 and the subject's eye 108, and the like can be performed, and distances of the reference light and the observation light are also adjusted.

Meanwhile, the observation light generated by the optical coupler 203 is transmitted through an optical fiber 208, an OCT-X scanner 113, and an OCT-Y scanner 112 to the eyepiece lens 107 illustrated in FIG. 1. The observation light is reflected and scattered on the retina of the subject's eye 108 and becomes to signal light. The signal light enters the optical fiber 208 again. The signal light guided to the optical coupler 203 via the optical fiber 208 interferers with the reference light, and collimated by a collimator lens 210 via the optical fiber 209. Then, the light is dispersed by a diffraction grating 311, and an image is formed on a one-dimensional sensor 213 by a lens 212. The one-dimensional sensor 213 can be a charge coupled device (CCD) sensor, a complementary metal-oxide semiconductor (CMOS) sensor, or the like. With this configuration, the signal generated by dispersing the interference light can be acquired from the one-dimensional sensor 213.

With reference to FIG. 1, a scan mechanism in the fundus image capturing apparatus according to the present exemplary embodiment is described. The observation light from the OCT unit 115 is collimated by a collimator lens 114, and passes through the OCT-X scanner 113 and the OCT-Y scanner 112. Then, the observation light is reflected by a mirror 111 and a beam splitter 106, passes through the eyepiece lens 107, and enters the subject's eye 108. The observation light entered the subject's eye 108 is reflected and scattered on the fundus, passes through the same optical path, and returns to the OCT unit 115.

Figure 3:
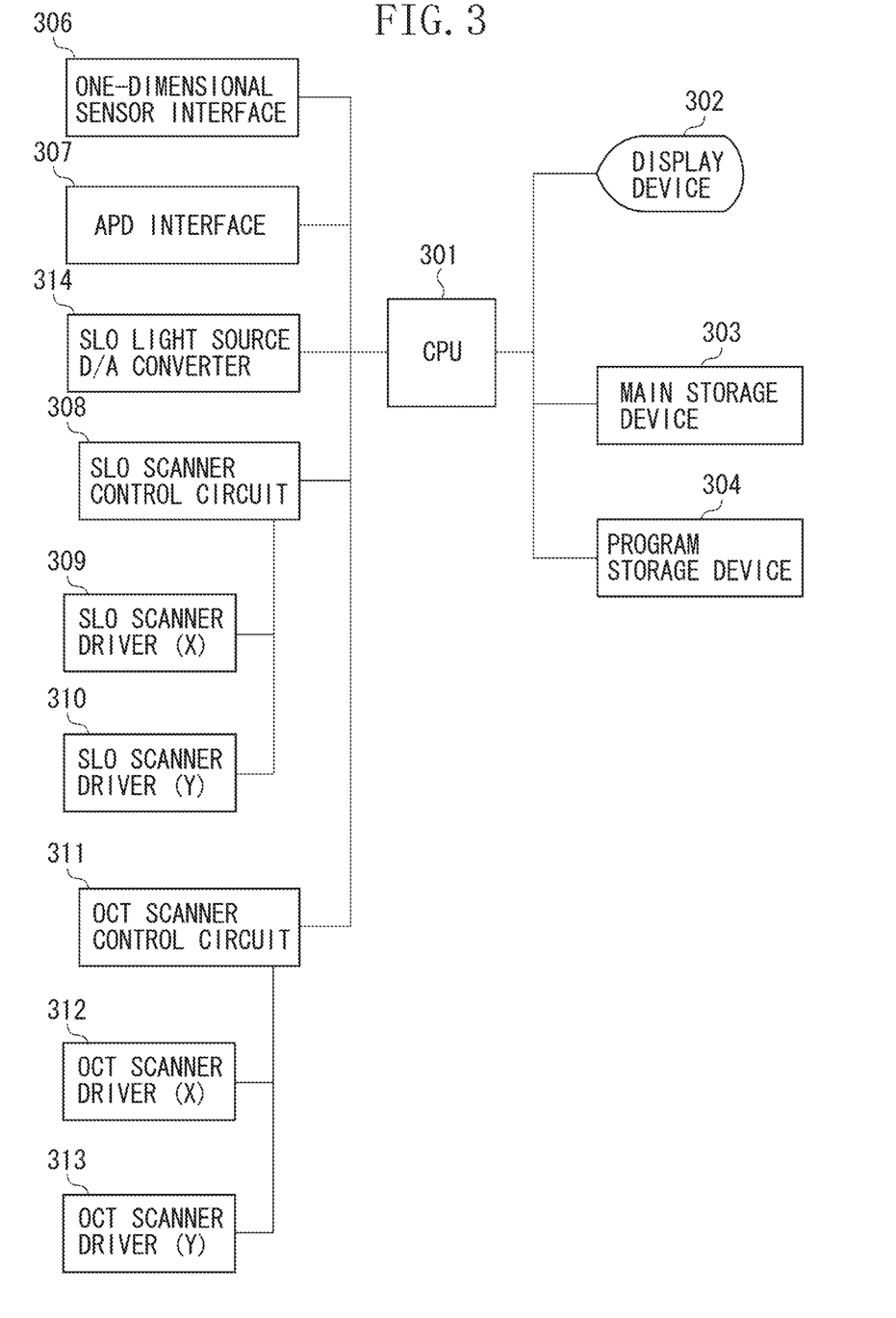
FIG. 3 is a view illustrating a configuration of a control device.

A control device for controlling the fundus image capturing apparatus illustrated in FIG. 1 is described with reference to FIG. 3. FIG. 3 is illustrates a configuration of the control device. In FIG. 3, the CPU 301 is connected with a display device 302, a main storage device 303 (i.e., a random access memory (RAM)), and a program storage device 304 (i.e., a read-only memory (ROM)). The CPU 301 is also connected with a one-dimensional sensor interface 306, an APD interface 307, and an SLO light source digital-to-analog (D/A) converter 314. The one-dimensional sensor interface 306 is used to input data, which is an output of the OCT unit 115, in a one-dimensional sensor 213. The APD interface 307 is used to input data of the APD 110, which is an output in the SLO method. The SLO light source D/A converter 314 generates voltage for controlling the strength of the light source (laser light source 101) in the SLO method.

The CPU 301 is further connected with a SLO scanner control circuit 308 and an OCT scanner control circuit 311 functioning as scanner controllers. The SLO scanner control circuit 308 controls the SLO-X scanner 104 using an SLO scanner driver (X) 309, and also controls the SLO-Y scanner 105 using an SLO scanner driver (Y) 310. The SLO scanner control circuit 308 controls a scan center position in the Y direction, a scan width in the Y direction, and a scan speed, in response to an instruction from the CPU 301. Further, the CPU 301 can identify a scan position of the laser beam based on an output from the SLO scanner control circuit 308.

The OCT scanner control circuit 311 controls the OCT-X scanner 113 using an OCT scanner driver (X) 312, and also controls the OCT-Y scanner 112 using an OCT scanner driver (Y) 313. The OCT scanner control circuit 311 controls the scan center positions in the X direction and the Y direction, the scan widths in the X direction and the Y direction, and the scan speed in response to an instruction from the CPU 301. Further, the CPU 301 can identify the scan position of the observation light based on an output from the OCT scanner control circuit 311. The CPU 301 can cause the fundus image capturing apparatus to function as described below by reading and executing a program for implementing the processing illustrated in FIG. 4, the program being stored in the program storage device 304.

The SLO imaging processing is described. The CPU 301 sets a predetermined value to the SLO light source D/A converter 314 and sets a predetermined scan center position in the Y direction, a predetermined scan width in the Y direction, and a predetermined scan speed to the SLO scanner control circuit 308. Thus, the CPU 301 controls the SLO scanner control circuit 308 to scan the fundus with the laser beam. At the same time, the APD 110 outputs a signal proportionate to the reflection/scattering strength of the retina. The signal output from the APD 110 is input to the CPU 301 via the APD interface 307. The CPU 301 superimposes the output signal from the APD 110 at the scan position of the laser beam, so that a fundus image can be acquired. The CPU 301 causes the display device 302 to display the fundus image.

The OCT imaging processing is described. The CPU 301 sets to the OCT scanner control circuit 311 the scan center positions in the X direction and the Y direction, the scan widths in the X direction and the Y direction, the scan speed, and a main scanning direction, and causes the OCT scanner control circuit 311 to scan the retina with the observation light from the OCT unit 115. At this point, the output of the one-dimensional sensor 213 in the OCT unit 115 is input to the CPU 301 via the one-dimensional sensor interface 306. The CPU 301 performs processing such as frequency-to-wave number conversion fast Fourier transform (FFT) in the main storage device 303 to acquire a depth direction of the retina. The CPU 301 can acquire a three-dimensional retinal image using the depth direction of the retina and the scan position of the observation light, and causes the display device 302 to display the three-dimensional retinal image.

Figure 4:
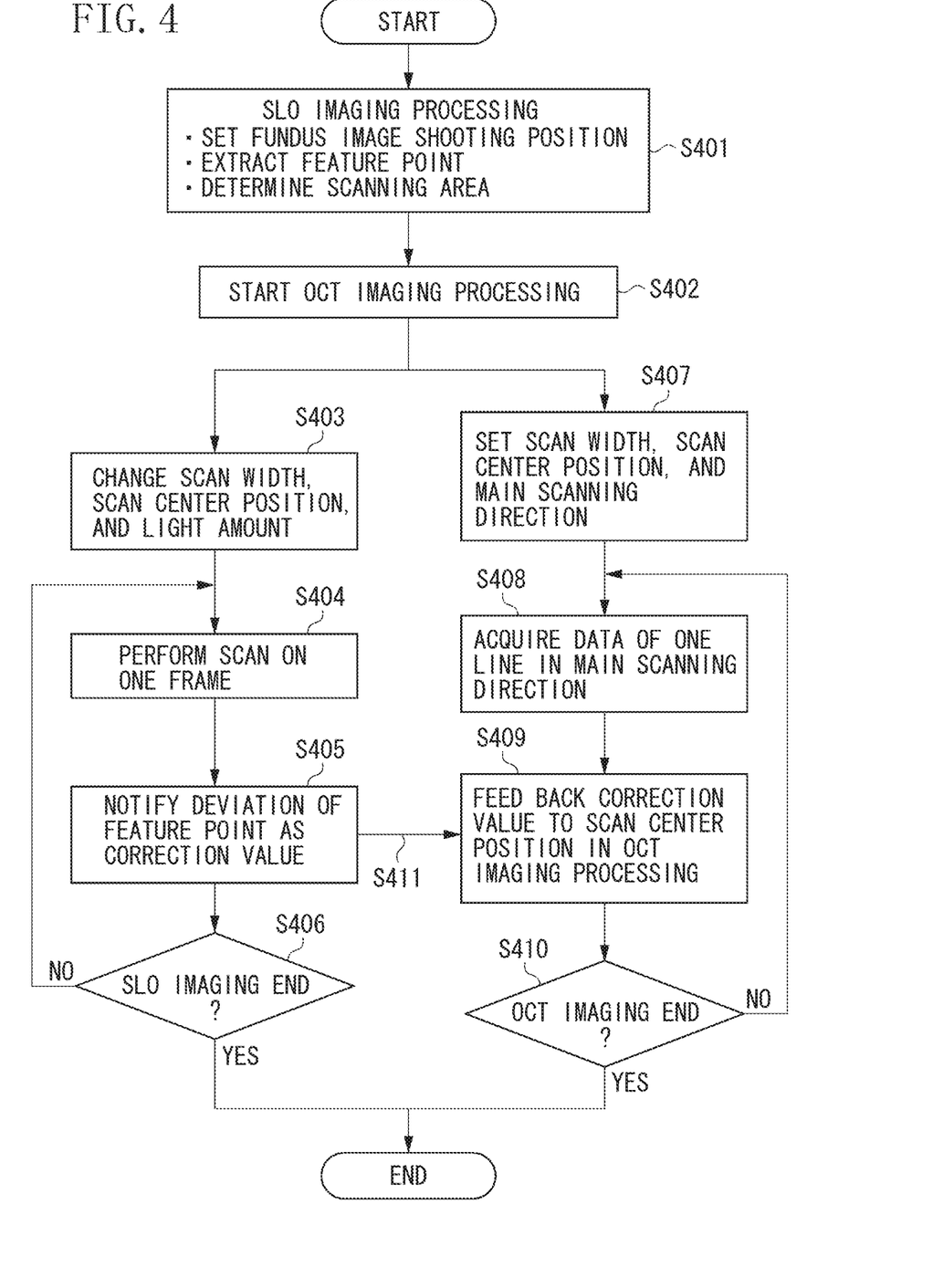
FIG. 4 is a flowchart illustrating processing performed by a control unit.
Figure 5:
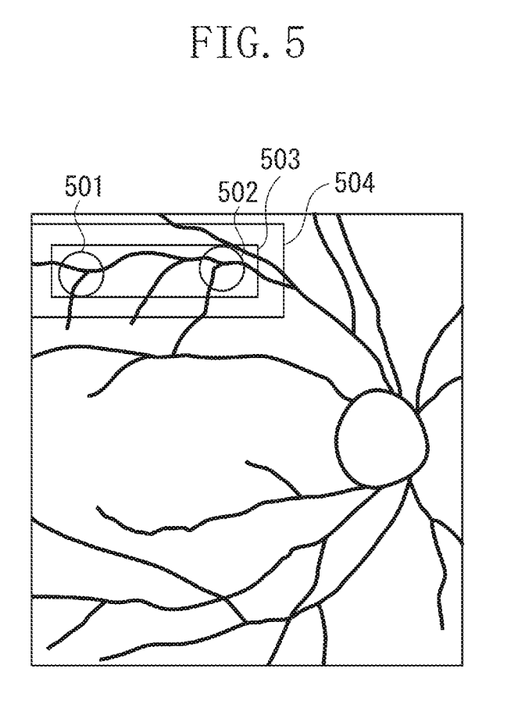
FIG. 5 is a view illustrating an example of branch points of blood vessels.

The processing performed by the control unit illustrated in FIG. 3 is described with reference to the flowchart in FIG. 4. In step S401, the CPU 301 captures a fundus image by the SLO imaging processing. More specifically, the CPU 301 sets the predetermined value to the SLO light source D/A converter 314, sets the predetermined scan center position in the Y direction, the predetermined scan width in the Y direction, and the predetermined scan speed to the SLO scanner control circuit 308, and causes the SLO scanner control circuit 308 to capture a fundus image. FIG. 5 illustrates an example of a fundus image acquired by the SLO imaging processing. In the fundus image illustrated in FIG. 5, the scan widths in the X direction and the Y direction are about 7 mm respectively. An examiner sets an imaging position of the fundus using such a fundus image.

Then, the CPU 301 extracts a feature point on the eye. The number of the feature points can be one when tracking is performed only in the X direction and the Y direction, however, the use of a plurality of feature points can increase the accuracy, and allows correction such as rotation. In the present exemplary embodiment, the tracking is performed in the X direction and the Y direction using two feature points. In the example in FIG. 5, branch points 501 and 502 of blood vessels are used as the feature points. The method for extracting the feature points is discussed in the above-described Japanese Patent Application Laid-Open No. 2001-70247, and accordingly, the description of the method is omitted.

Figure 6:
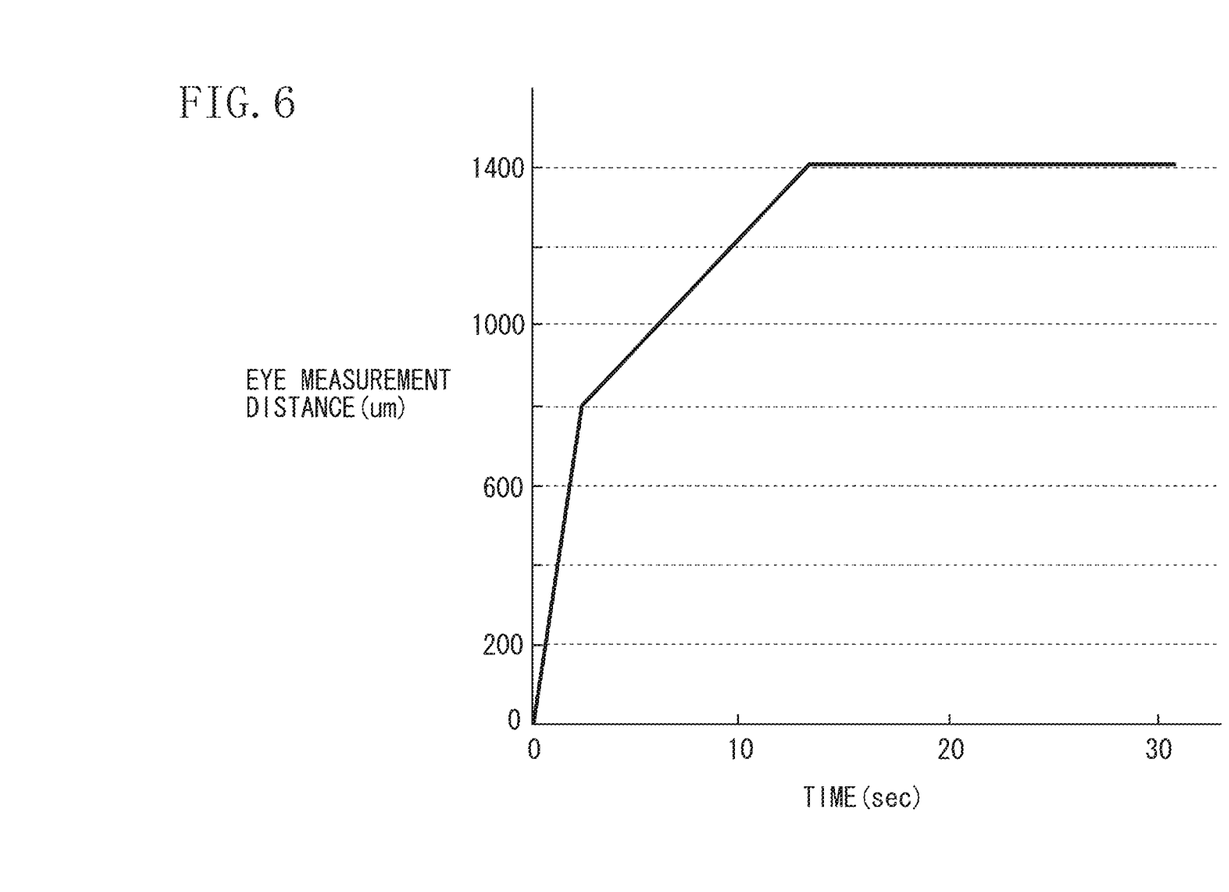
FIG. 6 is a view illustrating an example of typical movement of a human eye.

For the tracking, an area 503 containing these feature points is to be scanned. However, due to movement referred to as the involuntary eye movement during fixation, a larger area is to be scanned. FIG. 6 illustrates typical movement of a human eye. As illustrated in FIG. 6, in a case where the imaging takes 15 seconds or more, for example, the scanning area is to be expanded by ±1.4 mm in the X direction and the Y direction. The expanded area is an area 504. The CPU 301 determines the area 504 as the scanning area. As compared to the scan area at the time of the capturing the fundus image, the scanning area in the tracking is small. Thus, when the scan is performed at the same frame rate, the scan speed in the tracking can be reduced. Consequently, to irradiate the fundus at the same luminance in the capturing of the fundus image and in the tracking, the light amount in the tracking can be reduced according to an area ratio between the scanning area in the capturing of the fundus image and the scanning area in the tracking.

In step S402, the CPU 301 starts the OCT imaging processing. From this point of time, the SLO imaging processing and the OCT imaging processing are simultaneously performed. First, the SLO imaging processing for tracking is described.

In step S403, the CPU 301 changes the scan center point in the Y direction and the scan width in the Y direction with respect to the SLO scanner control circuit 308 to values corresponding to the scanning area 504 calculated in step S401. Further, the CPU 301 sets the light amount to a small value proportionate to the area of the scanning area 504.

In step S404, the CPU 301 performs one frame scan on the scanning area 504. In step S405, the CPU 301 detects deviations from the previous feature points using a pattern matching method or the like, and notifies the OCT imaging processing of the deviation values as correction values by communication (in step S411).

In step S406, the CPU 301 determines whether the SLO imaging processing ends. If the SLO imaging processing has not ended (NO in step S406), the processing returns to step S404. Whereas if the SLO imaging processing ends (YES in step S406), the processing ends.

The processing for changing the imaging area in step S403 is started in response to the start of the OCT imaging processing, however, the present exemplary embodiment is not limited to this configuration. Alternatively, the SLO imaging range can be changed after focus adjustment is ended or adjustment of the coherence gate position is ended in the OCT imaging processing.

The SLO imaging range can be changed immediately after the focus in the SLO is appropriately set. In such a case, the CPU 301 controls the SLO scanner control circuit 308 such that the imaging range is to be expanded once in several frames, and causes the display device 302 to display the acquired image of the expanded imaging range. By this processing, the examiner can appropriately refer to a planer image perpendicular to the optical axis of the fundus.

In another example, the observation by the SLO and the accurate imaging by the OCT can be simultaneously performed by determining the OCT imaging range after the start of the SLO imaging or changing the SLO imaging range in response to determination of the OCT imaging position by specifying the center of the imaging position or the like. Further, in yet another example, if the tracking is accurately performed by changing the SLO imaging range after a shooting button is pressed, and the OCT imaging is performed, then the examiner can check the SLO image at a higher frame rate.

The OCT imaging processing is described. In step S407, the CPU 301 sets to the OCT control circuit 311 the scan center positions in the X direction and the Y direction, the scan widths in the X direction and the Y direction, and the main scanning direction. In step S408, the CPU 301 acquires data of one line in the main scanning direction.

In step S409, the CPU 301 feeds back the correction value transmitted by the communication (step S411) to the scan center position in the OCT imaging processing.

In step S410, the CPU 301 determines whether the OCT imaging processing ends. If the OCT imaging processing has not ended (NO in step S410), the processing returns to step S408. If the OCT imaging processing ends (YES in step S410), the processing ends. When the OCT imaging processing ends, in the determination in the next step S406, it is determined that the SLO imaging processing also ends.

As described above, according to the present exemplary embodiment, the movement of the fundus detected by the SLO imaging processing is fed back to the OCT imaging processing. Thus, the OCT imaging processing with the corrected fundus movement can be performed.

In the above-described exemplary embodiment, it is assumed that the frame rate is constant, and the light amount in the SLO imaging processing in the tracking is reduced in proportion to the area of the scanning area. Alternatively, if the light amount in the OCT imaging processing is enough, the frame rate can be increased without reducing the light amount. Accordingly, further accurate tracking can be performed. Alternatively, both of the values can be controlled halfway, that is, the frame rate is slightly increased and the light amount is correspondingly reduced.

For example, if the deviations of the feature points detected in step S405 are large (that is, the eye movement is large), the frame rate is increased and the light amount is reduced correspondingly. On the other hand, if the deviations of the feature points detected in step S405 are small (that is, the eye movement is small), the frame rate is reduced and the light amount is increased correspondingly.

It is possible to associate the magnitude of movement of the eye, the reflectivity of the eye, the light amount in the SLO imaging processing, the frame rate in the tracking, and an evaluation value of a finally acquired image quality in a table. With reference to the table, for example, when the movement of the eye is large, the frame rate is increased to prioritize the accuracy of the tracking, and the image quality can be increased. Meanwhile, when the reflectivity of the eye is low, the light amount is increased to prioritize the light amount in the SLO imaging, and the image quality can be increased.

In the above-described exemplary embodiment, the branch points of the blood vessels are used for the feature points. However, the subject can slightly see the branch points if infrared light is used. As a result, the visual fixation of the subject's eye may not be stable. To solve this issue, the optic papilla can be used. The subject cannot see the optic papilla, so that stable visual fixation can be expected.

In the above-described exemplary embodiment, the positional deviation is detected by the pattern matching using the feature points. However, the method is not limited to the above, the CPU 301 can employ a pattern matching using a degree of similarity of pixel values of an image. The processing speed of the positional deviation detection processing using the feature points is fast. Consequently, it is preferable to use the processing when the processing capability is poor, or when the frame rate of the SLO moving image capturing is relatively high. On the other hand, the positional deviation detection processing using the degree of similarity is accurate. Consequently, it is preferable to use the processing when the processing capability is high and the frame rate is relatively low.

In the above-described exemplary embodiment, sometimes it takes several seconds to capture images, for example, when a high-resolution three-dimensional fundus image is acquired. During the processing, the display of the fundus image is not updated. To solve this issue, the SLO imaging processing for acquiring a fundus image in step S401 can be performed once in a plurality of times of the processing of the SLO imaging for tracking.

More specifically, the CPU 301 controls the SLO scanner control circuit 308 such that the SLO imaging range is expanded to the imaging range before the start of the tracking once in several frames and image capturing processing is performed. Further, the CPU 301 updates the SLO image displayed on the display device 302 with the SLO image captured by expanding the imaging range. Due to the change of the imaging range, the constant frame rate in the SLO is lost, however, the fundus image is displayed on the display device 302 at a repetition rate smaller than at least an average repetition rate in the SLO imaging. By this processing, the fundus image for observation is appropriately captured and displayed. Thus, the state of the fundus can be displayed in real time while the tracking accuracy is increased.

In the above-described exemplary embodiment, both of the control for making the imaging area in the tracking smaller than the imaging area of the fundus image for observation, and the control for reducing the light amount in the tracking than the light amount in the capturing of the fundus image for observation are performed. However, either one of the control can be performed. For example, if the CPU 301 performs the control such that the imaging area is set to a small area and the light amount is not changed, the S/N ratio of the SLO image for tracking can be maintained at a high level. Alternatively, if the CPU 301 performs the control such that only the light amount is reduced and the imaging range is not changed, the imaging area used for the positional deviation detection can be expanded.

Further, the CPU 301 can determine whether to respectively perform the setting of reducing the imaging area and the setting of reducing the light amount according to an input of the user via an operation unit (not illustrated), and the CPU 301 can determine to perform both of the processes respectively. By this processing, the tracking accuracy and the S/N ratio of the image can be controlled as required by the user, and an image desired by the user can be acquired.

In another exemplary embodiment, in a case where an SLO image and an OCT image captured prior to a main image capturing in the OCT are provided, the CPU 301 calculates image qualities of the images using an index such as an S/N ratio, and determines whether the quality of the OCT image in the main image capturing is enough in consideration of superimposition, noise removal processing, and the like. As a result of the determination, if an adequate image quality can be ensured, the setting of reducing the imaging area of the SLO image for tracking and the setting of reducing the light amount are not performed. By this processing, the tracking accuracy can be maintained, and a high-quality image can be acquired.

In the above-described exemplary embodiments, the light amount for tracking can be reduced. Consequently, the reduction of the light amount for the OCT imaging processing can be suppressed to a minimum, and the deterioration of the fundus image can be prevented. Further, at the same time, the tracking rate can be increased, and consequently, the tracking accuracy can be increased.

Embodiment of the present invention can also be realized by a computer of a system or apparatus (or devices such as a CPU or an MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium).

While the embodiment of the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-155870 filed Jul. 14, 2011, which is hereby incorporated by reference herein in its entirety.

What is claimed is:

1. An imaging control apparatus capable of causing a first imaging unit to capture a fundus image of a subject's eye and causing a second imaging unit to capture a tomographic image of the subject's eye, the imaging control apparatus comprising:
    a display control unit configured to display a first fundus image on a display unit, the first fundus image being captured by the first imaging unit in a first area on a fundus of the subject's eye;
    an extraction unit configured to extract one or more feature points from the first fundus image;
    an area determination unit configured to determine a second area on the fundus of the subject's eye, the second area including the one or more feature points and being smaller than the first area;
    a control unit configured to cause the first imaging unit to capture a second fundus image of the subject's eye in the second area;
    a detection unit configured to detect a positional deviation of the fundus of the subject's eye by comparing the first fundus image and the second fundus image; and
    a correction unit configured to correct an image capturing position of the second imaging unit for capturing the tomographic image based on the detected positional deviation.

2. The imaging control apparatus according to claim 1, wherein the control unit causes the first imaging unit to capture the second fundus image of the subject's eye in the second area, and in a light amount lower than a light amount used for the image capturing of the first fundus image in the first area.

3. The imaging control apparatus according to claim 1, further comprising
    a light control unit configured to cause the first imaging unit to capture a first fundus image of the subject's eye in a first light amount and a second fundus image of the subject's eye in a second light amount, the second light amount being lower than the first light amount.

4. The imaging control apparatus according to claim 1, further comprising a first control unit configured to control at least one of a frame rate and a light amount at image capturing by the first imaging unit based on the positional deviation detected by the detection unit.

5. The imaging control apparatus according to claim 1, further comprising a second control unit configured to control a light amount at image capturing by the first imaging unit based on reflectivity of the fundus of the subject's eye.

6. The imaging control apparatus according to claim 1, wherein the detection unit detects a position of an optic papilla of the subject's eye as the position of the feature point.

7. The imaging control apparatus according to claim 1, wherein a part of a plurality of image capturing processes for detecting the position deviation by the detection unit is performed as an image capturing process for capturing the fundus image of the subject's eye in the first area.

8. The imaging control apparatus according to claim 1, wherein the first imaging unit is a scanning laser ophthalmoscope.

9. The imaging control apparatus according to claim 1, wherein the second imaging unit is an optical coherence tomography apparatus.

10. An ophthalmic imaging apparatus comprising:
    an imaging control apparatus according to claim 1,
    the first imaging unit; and
    the second imaging unit.

11. The imaging control apparatus according to claim 1, further comprising a repeat control unit configured to repeat capturing the second fundus image by controlling of the control unit, detecting the positional deviation by the detection unit and correcting the image capturing position by the correction unit.

12. An imaging control apparatus capable of causing a first imaging unit to capture a first fundus image in a first area of a subject's eye and causing a second imaging unit to capture a tomographic image of the subject's eye, the imaging control apparatus comprising:
    an extraction unit configured to extract one or more feature points from the first fundus image;
    an area determination unit configured to determine a second area on the fundus of the subject's eye, the second area including the one or more feature points and being smaller than the first area;
    a control unit configured to cause the first imaging unit to capture a second fundus image of the subject's eye the second area;
    a detection unit configured to detect a movement of the subject's eye by comparing the first fundus image and the second fundus image; and
    a determination unit configured to determine an image capturing position of the second imaging unit for capturing the tomographic image based on the detected movement.

13. The imaging control apparatus according to claim 12, further comprising a repeat control unit configured to repeat capturing the second fundus image by controlling of the control unit, detecting the positional deviation by the detection unit and determining the image capturing position by the determination unit.

14. A method for controlling image capturing performed by an imaging control apparatus capable of causing a first imaging unit to capture a fundus image of a subject's eye and causing a second imaging unit to capture a tomographic image of the subject's eye, the method comprising:
   displaying a first fundus image on a display unit, the first fundus image being captured by the first imaging unit in a first area on a fundus of the subject's eye;
   extracting one or more feature points from the first fundus image;
   determining a second area on the fundus of the subject's eye, the second area including the one or more feature points and being smaller than the first area;
   causing the first imaging unit to capture a second fundus image of the subject's eye in the second area;
   detecting a positional deviation of the fundus of the subject's eye by comparing the first fundus image and the second fundus image; and
   correcting an image capturing position of the tomographic image of the second imaging unit for capturing the tomographic image based on the detected positional deviation.

15. The method according to claim 14, further comprising:
   causing the first imaging unit to capture a first fundus image of the subject's eye in a first light amount and a second fundus image of the subject's eye in a second light amount, the first light amount being lower than the second light amount.

16. A program for causing a computer to execute a method for controlling image capturing performed by an imaging control apparatus capable of causing a first imaging unit to capture a fundus image of a subject's eye and causing a second imaging unit to capture a tomographic image of the subject's eye, the program comprising:
   displaying a first fundus image on a display unit, the first fundus image being captured by the first imaging unit in a first area on a fundus of the subject's eye;
   extracting one or more feature points from the first fundus image;
   determining a second area on the fundus of the subject's eye, the second area including the one or more feature points and being smaller than the first area;
   causing the first imaging unit to capture a second fundus image of the subject's eye in the second area;
   detecting a positional deviation of the fundus of the subject's eye by comparing the first fundus image and the second fundus image; and
   correcting an image capturing position of the tomographic image of the second imaging unit for capturing the tomographic image based on the detected positional deviation.

17. The program according to claim 16, further comprising:
   causing the first imaging unit to capture a first fundus image of the subject's eye in a first light amount and a second fundus image of the subject's eye in a second light amount, the first light amount being lower than the second light amount.

* * * * *